United States Patent
Friends et al.

(10) Patent No.: US 7,109,164 B2
(45) Date of Patent: Sep. 19, 2006

(54) ANILINE-DERIVED LIGANDS FOR THE THYROID RECEPTOR

(75) Inventors: Todd J. Friends, Hamilton, NJ (US); Denis E. Ryono, Princeton, NJ (US); Minsheng Zhang, Warren, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 44 days.

(21) Appl. No.: 10/930,360

(22) Filed: Aug. 30, 2004

(65) Prior Publication Data
US 2005/0032890 A1  Feb. 10, 2005

Related U.S. Application Data

(62) Division of application No. 09/761,050, filed on Jan. 16, 2001, now Pat. No. 6,800,605.

(60) Provisional application No. 60/183,223, filed on Feb. 17, 2000.

(51) Int. Cl.
C07C 37/00 (2006.01)
(52) U.S. Cl. .................... 514/2; 514/576; 514/577; 514/717; 514/730; 514/736; 568/579; 568/583; 568/585; 568/588; 568/626; 568/630; 568/635
(58) Field of Classification Search .................... None
See application file for complete search history.

(56) References Cited

U.S. PATENT DOCUMENTS

| 5,401,772 | A | 3/1995 | Yokoyama et al. |
| 6,194,454 | B1 | 2/2001 | Dow |
| 2001/0051657 | A1 | 12/2001 | Chiang et al. |

FOREIGN PATENT DOCUMENTS

| DE | 1078582 B | 3/1960 |
| EP | 0580550 | 10/1997 |
| EP | 1088819 | 4/2001 |
| WO | WO 99 00353 | 1/1999 |
| WO | WO 00/51971 | 8/2000 |
| WO | WO 00/58279 | 10/2000 |
| WO | WO 01/85670 A1 | 11/2001 |

OTHER PUBLICATIONS

Dermer, Gerald 'Another Anniversary for the War on Cancer' Bio/technology, vol. 12, Mar. 1994, p. 320.*
Gura, Trisha 'Systems of Identifying New Drugs are Often Faulty' Science, vol. 278, Nov. 1997, pp. 1041-1042.*
Golden, Fredrick, 'Of Mice and Men Don't Blame the Rodents.' Time, May 1997, pp. 44.*
The Merck Manual (ed. R. Berkow), 'Scaling Papular Disease', Ch. 239, pp. 2435-2439, Sixth ed., 1992.*
File medline on STN. AN No. 90150816. Zugerman, C. 'Chloracne. Clinical Manifestatoin and Etiology', Dermat. Clin. Jan. 1990, vol. 8, No. 1, pp. 209-213. Abstract only. Abstract date 1990.*
The Merck Manual, 'Keloid' [online retrived on Dec. 13, 2003]. Retrived from the internet <http://www.merck.com/mrkshared/mmanual/section10/chapter125/125k.jsp>.*
"Computerized Drug Design: Still Promising, Not Yet Here", Science, vol. 256, pp. 441, Apr. 24, 1992.*
Yokoyama, N., J. Med. Chem., vol. 38, pp. 695-707, 1995.

* cited by examiner

Primary Examiner—Anish Gupta
(74) Attorney, Agent, or Firm—Sammy G. Duncan, Jr.

(57) ABSTRACT

New thyroid receptor ligands are provided which have the general formula

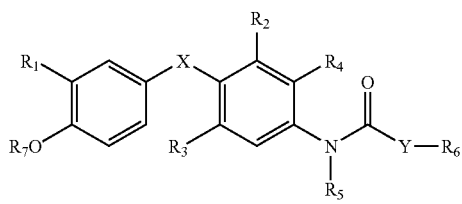

in which:
X is —O—, —S—, —CH$_2$—, —CO—, or —NH—;
Y is —(CH$_2$)$_n$— where n is an integer from 1 to 5, or cis- or trans-ethylene;
R$_1$ is halogen, trifluoromethyl, or alkyl of 1 to 6 carbons or cycloalkyl of 3 to 7 carbons;
R$_2$ and R$_3$ are the same or different and are hydrogen, halogen, alkyl of 1 to 4 carbons or cycloalkyl of 3 to 6 carbons, at least one of R$_2$ and R$_3$ being other than hydrogen;
R$_4$ is hydrogen or lower alkyl;
R$_5$ is hydrogen or lower alkyl;
R$_6$ is carboxylic acid, or esters or prodrugs;
R$_7$ is hydrogen or an alkanoyl or an aroyl.

In addition, a method is provided for preventing, inhibiting or treating a disease associated with metabolism dysfunction or which is dependent upon the expression of a T$_3$ regulated gene, wherein a compound as described above is administered in a therapeutically effective amount. Examples of such diseases associated with metabolism dysfunction or are dependent upon the expression of a T$_3$ regulated gene include obesity, hypercholesterolemia, atherosclerosis, cardiac arrhythmias, depression, osteoporosis, hypothyroidism, goiter, thyroid cancer as well as glaucoma, congestive heart failure and skin disorders.

12 Claims, No Drawings

ANILINE-DERIVED LIGANDS FOR THE THYROID RECEPTOR

This application is a Divisional of U.S. patent application Ser. No. 09/761,050, filed Jan. 16, 2001 now U.S. Pat. No. 6,800,605 that claim priority from U.S. Provisional Application No. 60/183,223, filed Feb. 17, 2000.

FIELD OF THE INVENTION

This invention relates to novel compounds which are thyroid receptor ligands, and are preferably selective for the thyroid hormone receptor β, and to methods of preparing such compounds and to methods for using such compounds such as in the regulation of metabolism.

BACKGROUND OF THE INVENTION

While the extensive role of thyroid hormones in regulating metabolism in humans is well recognized, the discovery and development of new specific drugs for improving the treatment of hyperthyroidism and hypothyroidism has been slow. This has also limited the development of thyroid agonists and antagonists for treatment of other important clinical indications, such as hypercholesterolemia, obesity and cardiac arrhythmias.

Thyroid hormones affect the metabolism of virtually every cell of the body. At normal levels, these hormones maintain body weight, the metabolic rate, body temperature, and mood, and influence serum low density lipoprotein (LDL) levels. Thus, in hypothyroidism there is weight gain, high levels of LDL cholesterol, and depression. In excess with hyperthyroidism, these hormones lead to weight loss, hypermetabolism, lowering of serum LDL levels, cardiac arrhythmias, heart failure, muscle weakness, bone loss in postmenopausal women, and anxiety.

Thyroid hormones are currently used primarily as replacement therapy for patients with hypothyroidism. Therapy with L-thyroxine returns metabolic functions to normal and can easily be monitored with routine serum measurements of levels of thyroid-stimulating hormone (TSH), thyroxine (3,5,3′,5′-tetraiodo-L-thyronine, or $T_4$) and triiodothyronine (3,5,3′-triiodo-L-thyronine, or $T_3$). However, replacement therapy, particularly in older individuals is limited by certain of the deleterious effects of thyroid hormones.

In addition, some effects of thyroid hormones may be therapeutically useful in non-thyroid disorders if adverse effects can be minimized or eliminated. These potentially useful influences include weight reduction, lowering of serum LDL levels, amelioration of depression and stimulation of bone formation. Prior attempts to utilize thyroid hormones pharmacologically to treat these disorders have been limited by manifestations of hyperthyroidism, and in particular by cardiovascular toxicity.

Development of specific and selective thyroid hormone receptor agonists could lead to specific therapies for these common disorders while avoiding the cardiovascular and other toxicities of native thyroid hormones. Tissue-selective thyroid hormone agonists may be obtained by selective tissue uptake or extrusion, topical or local delivery, targeting to cells through other ligands attached to the agonist and targeting receptor subtypes. Thyroid hormone receptor agonists that interact selectively with the β-form of the thyroid hormone receptor offers an especially attractive method for avoiding cardio-toxicity.

Thyroid hormone receptors (TRs) are, like other nuclear receptors, single polypeptide chains. The various receptor forms appear to be products of two different genes α and β. Further isoform differences are due to the fact that differential RNA processing results in at least two isoforms from each gene. The $TR\alpha_1$, $TR\beta_1$ and $TR\beta_2$ isoforms bind thyroid hormone and act as ligand-regulated transcription factors. In adults, the $TR\beta_1$ isoform is the most prevalent form in most tissues, especially in the liver and muscle. The $TR\alpha_2$ isoform is prevalent in the pituitary and other parts of the central nervous system, does not bind thyroid hormones, and acts in many contexts as a transcriptional repressor. The $TR\alpha_1$ isoform is also widely distributed, although its levels are generally lower than those of the $TR\beta_1$ isoform. This isoform may be especially important for development. Whereas many mutations in the TRβ gene have been found and lead to the syndrome of generalized resistance to thyroid hormone, mutations leading to impaired TRα function have not been found.

A growing body of data suggest that many or most effects of thyroid hormones on the heart, and in particular on the heart rate and rhythm, are mediated through the α-form of the $TR\alpha_1$ isoform, whereas most actions of the hormone such as on the liver, muscle and other tissues are mediated more through the β-forms of the receptor. Thus, a TRβ-selective agonist might not elicit the cardiac rhythm and rate influences of the hormones but would elicit many other actions of the hormones. It is believed that the α-form of the receptor is the major drive to heart rate for the following reasons:

1) tachycardia is very common in the syndrome of generalized resistance to thyroid hormone in which there are defective TRβ-forms, and high circulating levels of $T_4$ and $T_3$;
2) there was a tachycardia in the only described patient with a double deletion of the TRβ gene (Takeda et al, J. Clin. Endrocrinol. & Metab. 1992, Vol. 74, p. 49);
3) a double knockout TRα gene (but not β-gene) in the mouse has a slower pulse than control mice; and,
4) western blot analysis of human myocardial TRs show presence of the $TR\alpha_1$, $TR\alpha_2$ and $TR\beta_2$ proteins, but not $TR\beta_1$.

If these indications are correct, then a TRβ-selective agonist could be used to mimic a number of thyroid hormone actions, while having a lesser effect on the heart. Such a compound may be used for: (1) replacement therapy in elderly subjects with hypothyroidism who are at risk for cardiovascular complications; (2) replacement therapy in elderly subjects with subclinical hypothyroidism who are at risk for cardiovascular complications; (3) obesity; (4) hypercholesterolemia due to elevations of plasma LDL levels; (5) depression; and, (6) osteoporosis in combination with a bone resorption inhibitor.

DESCRIPTION OF THE INVENTION

In accordance with the present invention, compounds are provided which are thyroid receptor ligands, and have the general formula I:

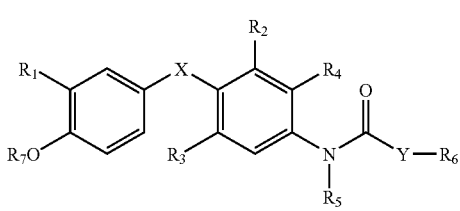

in which:

X is oxygen (—O—), sulfur (—S—), methylene(—CH$_2$—), carbonyl (—CO—), or —NH—;

Y is —(CH$_2$)$_n$— where n is an integer from 1 to 5, or —C═C— which may be cis or trans (also referred to as cis- or trans-ethylene);

R$_1$ is halogen, trifluoromethyl, or alkyl of 1 to 6 carbons or cycloalkyl of 3 to 7 carbons;

R$_2$ and R$_3$ are the same or different and are hydrogen, halogen, alkyl of 1 to 4 carbons or cycloalkyl of 3 to 6 carbons, at least one of R$_2$ and R$_3$ being other than hydrogen;

R$_4$ is hydrogen or lower alkyl;

R$_5$ is hydrogen or lower alkyl;

R$_6$ is carboxylic acid, or an ester thereof (preferably an alkyl ester), or a prodrug thereof;

R$_7$ is hydrogen or an alkanoyl or aroyl (such as acetyl or benzoyl) or other group capable of bioconversion to generate the free phenol structure (wherein R$_7$═H);

including all stereoisomers thereof, prodrug esters thereof, and pharmaceutically acceptable salts thereof.

In addition, in accordance with the present invention, a method for preventing, inhibiting or treating a disease associated with metabolism dysfunction or which is dependent upon the expression of a T$_3$ regulated gene is provided, wherein a compound of formula I is administered in a therapeutically effective amount. The compound of formula I is preferably an agonist that is preferably selective for the thyroid hormone receptor-beta. Examples of such diseases associated with metabolism dysfunction or are dependent upon the expression of a T$_3$ regulated gene are set out hereinafter and include obesity, hypercholesterolemia, atherosclerosis, cardiac arrhythmias, depression, osteoporosis, hypothyroidism, goiter, thyroid cancer as well as glaucoma and congestive heart failure.

DETAILED DESCRIPTION OF THE INVENTION

The following definitions apply to the terms as used throughout this specification, unless otherwise limited in specific instances.

The term "thyroid receptor ligand" as used herein is intended to cover any moiety which binds to a thyroid receptor. The ligand may act as an agonist, an antagonist, a partial agonist or a partial antagonist. Another term for "thyroid receptor ligand" is "thyromimetic".

Unless otherwise indicated, the term "lower alkyl", "alkyl" or "alk" as employed herein alone or as part of another group includes both straight and branched chain hydrocarbons, containing 1 to 12 carbons (in the case of alkyl or alk), in the normal chain, preferably 1 to 4 carbons, such as methyl, ethyl, propyl, isopropyl, butyl, t-butyl, or isobutyl, pentyl, hexyl, isohexyl, heptyl, 4,4-dimethylpentyl, octyl, 2,2,4-trimethylpentyl, nonyl, decyl, undecyl, dodecyl, which may be optionally substituted with 1 to 4 substituents which may include alkyl, alkenyl, alkynyl, aryl, cycloalkyl, heteroaryl, hydroxy, cyano, nitro, amino and/or carboxyl or alkyl ester thereof.

The term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may be optionally substituted through available carbon atoms with 1, 2, or 3 groups selected from hydrogen, halo, alkyl, haloalkyl, alkoxy, haloalkoxy, alkenyl, trifluoromethyl, trifluoromethoxy, alkynyl, hydroxy, amino, nitro, cyano and/or carboxyl or alkyl ester thereof.

The term "heteroaryl" or "heteroaromatic moiety" as used herein alone or as a part of another group refers to a 5- or 6-membered aromatic ring which includes 1, 2, 3, or 4 heteroatoms, one of which must be a nitrogen atom; the other atoms when present may be nitrogen, oxygen or sulfur, and such rings may be fused to another aryl or heteroaryl ring, and includes possible N-oxides. The heteroaryl group may optionally include 1 to 4 substituents such as aryl, alkyl, alkenyl, alkynyl, cycloalkyl, hydroxy, cyano, nitro, amino and/or carboxyl, or alkyl ester thereof.

Unless otherwise indicated, the term "lower alkenyl" or "alkenyl" as used herein by itself or as part of another group refers to straight or branched chain radicals of 2 to 12 carbons, preferably 2 to 5 carbons, in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and the like, which may be substituted as in the case of "alkyl".

Unless otherwise indicated, the term "lower alkynyl" or "alkynyl" as used herein by itself or as part of another group refers to straight or branched chain radicals of 2 to 12 carbons, preferably 2 to 8 carbons, in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, which may be substituted as in the case of "alkyl".

The term "alkanoyl" as employed herein alone or as part of another group is alkyl linked to a carbonyl group.

The term "aroyl" as employed herein alone or as part of another group is aryl linked to a carbonyl group.

Unless otherwise indicated, the term "cycloalkyl" as employed herein alone or as part of another group includes saturated cyclic hydrocarbon groups or partially unsaturated (containing 1 or 2 double bonds) cyclic hydrocarbon groups, containing one ring and a total of 3 to 7 carbons, preferably 3 to 6 carbons, forming the ring, which includes cyclopropyl, cyclobutyl, cyclopentyl, cyclohexyl, cycloheptyl, cyclopentenyl and cyclohexenyl, which may be substituted as in the case of "alkyl".

The term "halogen" or "halo" as used herein alone or as part of another group refers to chlorine, bromine, fluorine, and iodine as well as CF$_3$, with chlorine or bromine being preferred.

The (CH$_2$)$_n$ group is an alkylene group that includes 1 to 5 carbons in the normal chain which may include 1, 2, or 3 alkyl substituents.

Examples of (CH$_2$)$_n$ groups include

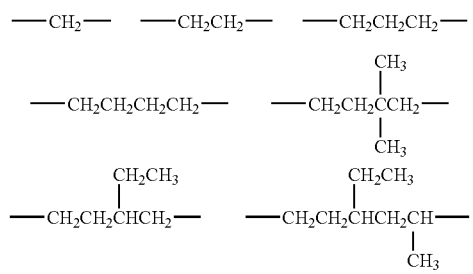

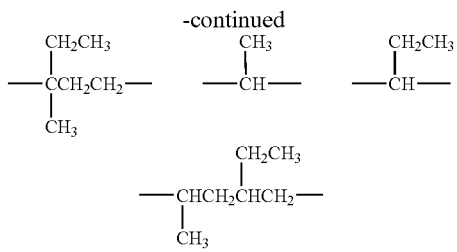

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C1–C4) alkyl or arylsulfonic acids which are unsubstituted or substituted, for example by halogen, for example methanesulfonic acid or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tertbutyl, diethyl, diisopropyl, triethyl, tributyl or dimethylpropylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I which include a basic group include monohydrochloride, hydrogensulfate, methanesulfonate, phosphate or nitrate.

Preferred salts of the compounds of formula I which include an acid group include sodium, potassium and magnesium salts and pharmaceutically acceptable organic amines.

Carboxylic acid prodrugs and prodrugs in general are described in standard references such as Chapter 31, written by Camille G. Wermuth et al., in "The Practice of Medicinal Chemistry", ed. C. G. Wermuth, Academic Press, 1996 (and the references contained therein).

Preferred prodrugs include lower alkyl esters such as ethyl ester, or acyloxyalkyl esters such as pivaloyloxymethyl (POM).

Preferred are compounds of the invention of formula I wherein X=O.

Further preferred compounds are those of formula I wherein X=O;

Y is cis- or trans-ethylene;

$R_1$ is halogen, trifluoromethyl, or alkyl of 1 to 6 carbons or cycloalkyl of 3 to 7 carbons;

$R_2$ and $R_3$ are independently bromo, chloro or methyl;

$R_4$ is hydrogen or methyl;

$R_5$ is hydrogen;

$R_6$ is carboxyl; and $R_7$ is hydrogen.

Other preferred compounds of the invention are those of formula I wherein X=O;

Y is —$(CH_2)_n$— where n is 1 or 2;

$R_1$ is halogen, trifluoromethyl, or alkyl of 1 to 6 carbons or cycloalkyl of 3 to 7 carbons;

$R_2$ and $R_3$ are independently bromo, chloro or methyl;

$R_4$ is hydrogen or methyl;

$R_5$ is hydrogen;

$R_6$ is carboxyl; and $R_7$ is hydrogen.

Most preferred are compounds of the invention of formula I wherein X=O;

Y is —$(CH_2)_n$— where n is 1;

$R_1$ is halogen, trifluoromethyl, or alkyl of 1 to 6 carbons or cycloalkyl of 3 to 7 carbons (most preferred being isopropyl);

$R_2$ and $R_3$ are independently bromo and chloro;

$R_4$ is hydrogen or methyl;

$R_5$ is hydrogen;

$R_6$ is carboxyl; and $R_7$ is hydrogen.

Thus, preferred compounds of the invention will have the structures:

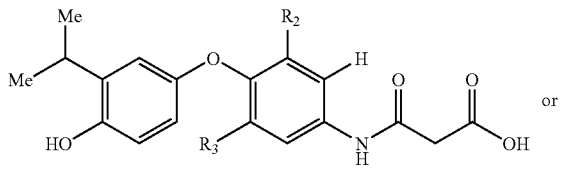

IA

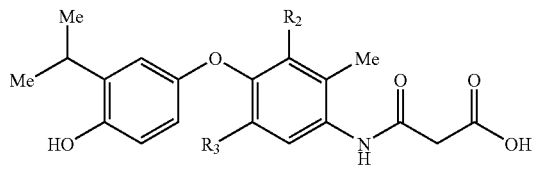

IB or an alkyl ester thereof.

Preferred compounds have the structures:

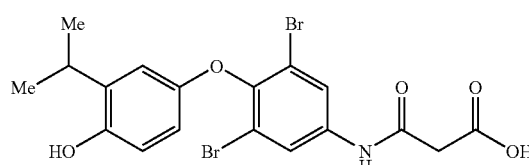

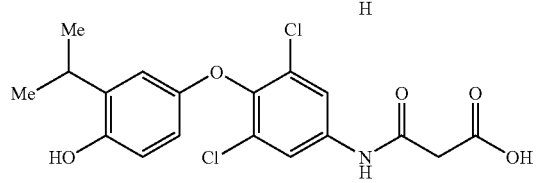

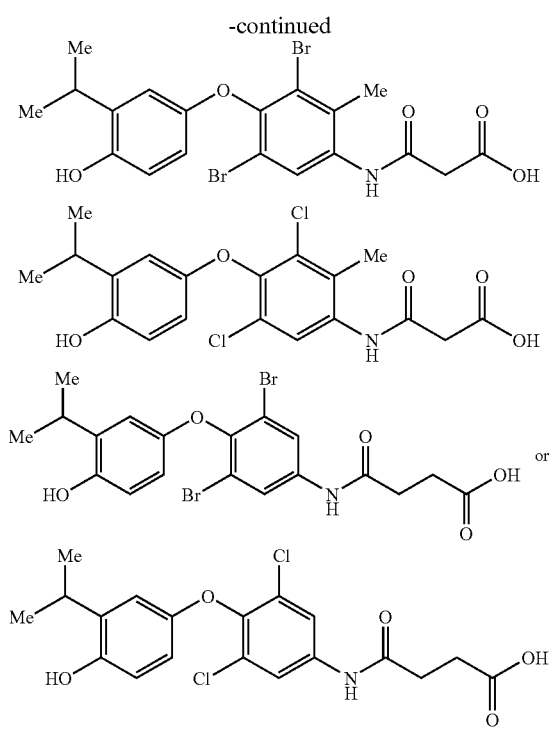

or alkyl esters thereof such as the methyl or ethyl ester thereof.

The most preferred compounds of the invention have the structures:

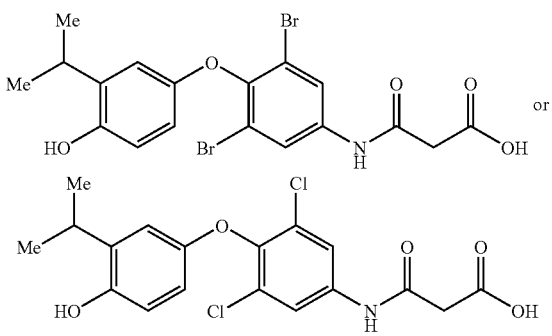

or alkyl esters thereof such as the methyl or ethyl ester.

The compounds of formula I may be prepared by the exemplary processes described in the following reaction schemes, as well as relevant published literature procedures that are used by one skilled in the art. Exemplary reagents and procedures for these reactions appear hereinafter and in the working Examples. Protection and deprotection in the Schemes below may be carried out by procedures generally known in the art (see, for example, T. W. Greene & P. G. M. Wuts, "Protecting Groups in Organic Synthesis", $3^{rd}$ Edition, Wiley, 1999).

Scheme 1 depicts a general synthetic approach to compounds of formula I for which X=O that utilizes the coupling of an appropriately substituted iodonium salt 1 to the appropriate phenol 2 to provide intermediate 3. In structure 1 and all other applicable structures contained in further schemes described below, PG refers to a protecting group appropriate for the functional group indicated (in this instance, for a phenolic oxygen). The specific protecting groups for each particular intermediate are well understood by those versed in the art (see also the reference, "Protecting Groups in Organic Synthesis", cited above). Subsequent protecting group and functional group manipulation provides the desired compounds of formula I. For example, intermediate 2 may be a nitrophenol (R' and R" are oxygen) and the resulting coupling product would be the corresponding diaryl ether nitro compound 3 where R'=R"=O. This nitro intermediate can be readily reduced to the corresponding aryl amine (see discussion below). The resulting aryl amine can then be readily acylated to provide the desired compounds of formula I (X=O). Intermediate 2 may also be a protected amino function, for example R'=$R_5$ and R"=PG. The protecting group (PG) may be carbamates such as t-butyloxycarbonyl (BOC) or benzyloxycarbonyl (CBZ), which may be later removed by acidolysis and/or hydrogenolysis under standard conditions. Acylation of the resulting aryl amine, again by means well-known to those versed in the art, provides the desired compounds of formula I. In addition, the aryl amine (intermediate 3 where R'=R"=H) resulting from reduction of a nitrobenzene coupling product can be reacted with an aldehyde in a reductive amination reaction, thus installing the group $R_5$ which comes from the aldehyde moiety. Reductive amination procedures, such as by the use of sodium cyanoborohydride or sodium triacetoxyborohydride, are well known to those skilled in the art. The resulting product can then be acylated by standard procedures to provide compounds of formula I.

Scheme 1

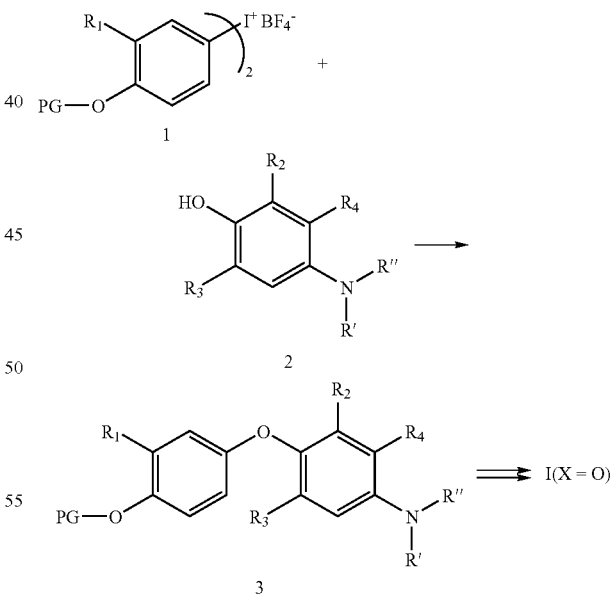

The iodonium salt methodology depicted in Scheme 1 is amply described in the literature for the synthesis of thyroid hormone analogs ("Novel Thyroid Receptor Ligands and Methods", Y.-L. Li, Y. Liu, A. Hedfors, J. Malm, C. Mellin, M. Zhang, PCT Int. App. WO 9900353 A1 990107; D. M. B. Hickey et al., J. Chem. Soc. Perkin Trans. I, 3103–3111, 1988; N. Yokoyama et al., J. Med. Chem., 38, 695–707, 1995), and to diaryl ethers in general (E. A. Couladouros, V. I. Moutsos, Tetrahedron Lett., 40, 7023–7026, 1999).

Scheme 2 depicts another general synthetic approach to compounds of formula I for which X=O in which an appropriately substituted nitrobenzene intermediate 5 is alkylated with an appropriately substituted phenol 4 to provide the nitro intermediate 6. The nitro function in intermediate 6 can be reduced to an amino group by methods well known in the art, such as the use of catalytic hydrogenation in the presence of, for example, Raney nickel or palladium on charcoal catalyst, in a polar solvent such as glacial acetic acid or ethanol. Alternatively, the reduction can be accomplished using iron powder in aqueous glacial acetic acid at ambient temperatures. Subsequent protecting group and functional group manipulation provides the desired compounds of formula I.

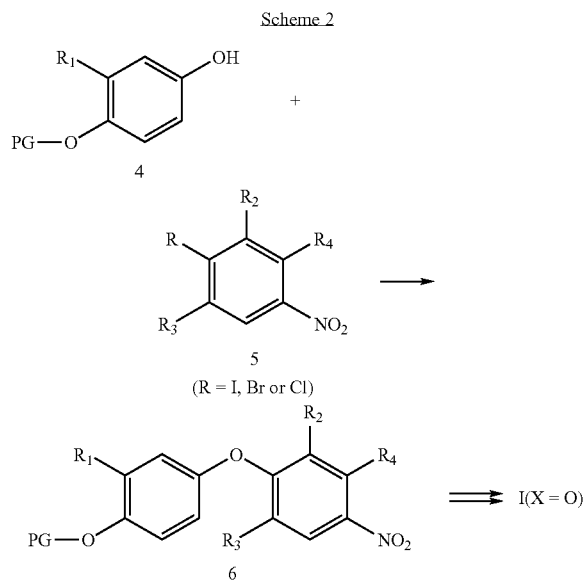

This approach depicted in Scheme 2 for the general synthesis of diaryl ethers for thyromimetics is well precedented in the literature (P. D. Leeson, J. C. Emmett, J. Chem. Perkin Trans. I, 3085–3096, 1988; N. Yokoyama et al., J. Med. Chem., 38, 695–707, 1995).

Further means for synthesizing compounds of formula I in which X=O, NH, S, CO or CH$_2$ are generally described in the literature (for X=O: D. M. B. Hickey et al., J. Chem. Soc. Perkin Trans. I, 3097–3102, 1988; Z.-W. Guo et al., J. Org. Chem., 62, 6700–6701, 1997; D. M. T. Chan et al., Tetrahedron Lett., 39, 2933–2936, 1998; D. A. Evans et al., Tetrahedron Lett., 39, 2937–2940, 1998; G. M. Salamonczyk et al., Tetrahedron Lett., 38, 6965–6968, 1997; J.-F. Marcoux, J. Am. Chem. Soc., 119, 10539–10540, 1997; A. V. Kalinin et al., J. Org. Chem., 64, 2986–2987, 1999; for X=N: D. M. T. Chan et al., Tetrahedron Lett., 39, 2933–2936, 1998; J. P. Wolfe et al., J. Am. Chem. Soc., 118, 7215, 1996; M. S. Driver, J. F. Hartwig, J. Am. Chem. Soc., 118, 7217, 1996; see references in the review by C. G. Frost, P. Mendonca, J. Chem. Soc. Perkin I, 2615–2623, 1998; for X=S: C. R. Harrington, Biochem. J., 43, 434–437, 1948; A. Dibbo et al., J. Chem. Soc., 2890–2902, 1961; N. Yokoyama et al., U.S. Pat. No. 5,401,772, 1995; for X=CO or CH$_2$: L. Horner, H. H. G. Medem, Chem. Ber., 85, 520–530, 1952; G. Chiellini et al., Chemistry & Biology, 5, 299–306, 1998).

Methods applicable to the synthesis of compounds of formula I in which X=O and R$_2$ and R$_3$ are independently varied as hydrogen, halogen and alkyl are described in "Novel Thyroid Receptor Ligands and Methods", Y.-L. Li, Y. Liu, A. Hedfors, J. Malm, C. Mellin, M. Zhang, PCT Int. App. WO 9900353 A1 990107.

Another general approach to the synthesis of compounds of formula I in which X=O is shown in Scheme 3. In this approach, an appropriately substituted iodonium salt 1 is coupled to the appropriately substituted 4-hydroxybenzoic acid intermediate 7. The carboxyl protecting group (PG') in the resulting coupling product 8 is then removed. The resulting free carboxylic acid intermediate corresponding to 8 is then subjected to a Curtius rearrangement by the use of known reagents for that transformation such as diphenylphosphoryl azide (DPPA). The Curtius rearrangement intermediate can be trapped by either t-butanol or benzyl alcohol to give the product 9, a t-butyloxycarbonyl (BOC) or a benzyloxycarbonyl (CBZ) protected aniline, respectively. These protecting groups can be removed by methods well known in the art to give the corresponding free amine group. The amine can then be acylated to give compounds of formula I with X=O by one of any number of well-established procedures, such as acylation with a free carboxylic acid by using a coupling reagent such as dicyclohexyl carbodiimide (DCC) or (1-[3-(dimethylamino)propyl]-3-ethylcarbodiimide (EDCI). Alternatively, the free amine can be acylated using a carboxylic acid chloride derivative in the presence of an equivalent amount of a tertiary organic amine such as triethylamine or N-methyl morpholine.

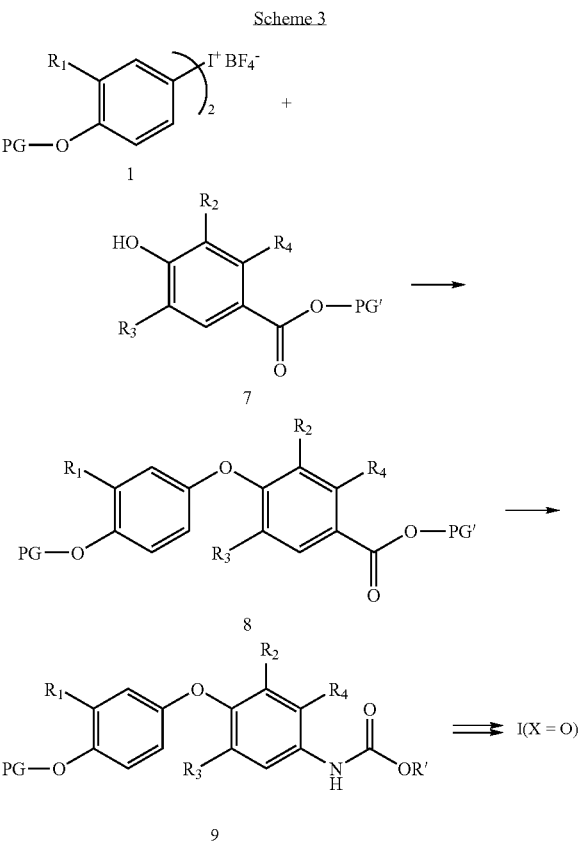

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The compounds of the invention are agonists, that are preferably selective for the thyroid hormone receptor-beta, and as such are useful in the treatment of obesity, hypercholesterolemia and atherosclerosis by lowering of serum LDL levels, alone or optionally in combination with a lipid modulating drug such as an HMG-CoA reductase inhibitor, fibrate, MTP inhibitor, squalene synthetase inhibitor and/or other hypolipidemic agent and/or optionally in combination with an antidiabetic agent; useful in the amelioration of depression, alone or optionally in combination with an antidepressant such as fluoxetine and desipramine; and useful in the stimulation of bone formation to treat osteoporosis, alone or optionally in combination with any known bone resorption inhibitor such as alendronate sodium. In addition, the compounds of the invention may be useful as replacement therapy in elderly patients with hypothyroidism or subclinical hypothyroidism who are at risk for cardiovascular complications, in the treatment of the elderly to provide a sense of well-being, and in the treatment of non-toxic goiter; in the management of papillary or follicular thyroid cancer (alone or with T4); in the treatment of skin disorders such as psoriasis, glaucoma, cardiovascular disease such as in the prevention or treatment of atherosclerosis, and congestive heart failure.

The compounds of the invention may be employed alone or in combination with an appetite suppressant such as sibutramine, and/or in combination with anti-obesity agents such as orlistat, and/or in combination with a β3 agonist, for treating obesity.

The compounds of the invention may also be used to treat skin disorders or diseases involving dermal atrophy such as glucocorticoid induced dermal atrophy, including restoration of dermal atrophy induced by topical glucocorticoids, the prevention of dermal atrophy induced by topical glucocorticoids (such as the simultaneous treatment with topical glucocorticoid or a pharmacological product including both glucocorticoid and a compound of the invention), the restoration/prevention of dermal atrophy induced by systemic treatment with glucocorticoids, restoration/prevention of atrophy in the respiratory system induced by local treatment with glucocorticoids, UV-induced dermal atrophy, or dermal atrophy induced by aging (wrinkles, etc.), wound healing, keloids, stria, cellulite, roughened skin, actinic skin damage, lichen planus, ichtyosis, acne, psoriasis, Dernier's disease, eczema, atopic dermatitis, chloracne, pityriasis and skin scarring.

In treating skin disorders or diseases as described above, the compounds of the invention may be used alone or optionally in combination with a retinoid such as tretinoin or a vitamin D analog, employing amounts as disclosed in the PDR.

The hypolipidemic agent which may be optionally employed in combination with the compounds of formula I of the invention may include thiazolidinediones, MTP inhibitors, HMG CoA reductase inhibitors, squalene synthetase inhibitors, fibric acid derivatives, ACAT inhibitors, cholesterol absorption inhibitors, ileal Na+/bile acid cotransporter inhibitors, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is

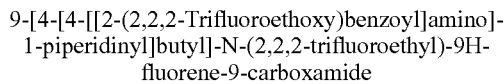

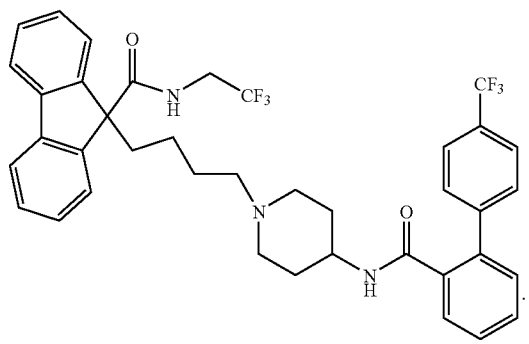

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, as well as other known HMG CoA reductase inhibitors.

In addition, phosphinic acid compounds useful in inhibiting HMG CoA reductase suitable for use herein are disclosed in GB 2205837.

The squalene synthetase inhibitors suitable for use herein include, but are not limited to, α-phosphonosulfonates disclosed in U.S. Pat. No. 5,712,396, those disclosed by Biller et al, J. Med. Chem., 1988, Vol. 31, No. 10, pp 1869–1871, including isoprenoid (phosphinylmethyl)phosphonates as well as other squalene synthetase inhibitors as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62.

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

Preferred hypolipidemic agents are pravastatin, lovastatin, simvastatin, atorvastatin, fluvastatin and cerivastatin.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolypidemic agent, the antidepressant, and/or bone resorption inhibitor and/or appetite suppressant (where present), within the range from about 500:1 to about 0.005:1, preferably from about 300:1 to about 0.01:1.

The antidiabetic agent which may be optionally employed in combination with compounds of formula I of the invention may include biguanides, sulfonyl ureas, glucosidase inhibitors, thiazolidinediones and/or aP2 inhibitors and/or PPAR α agonists, PPAR γ agonists or PPAR α/γ dual agonists, and/or SGLT2 inhibitors, or meglitinide.

The antidiabetic agent may be an oral antihyperglycemic agent preferably a biguanide such as metformin or phenformin or salts thereof.

Where the antidiabetic agent is a biguanide, the compounds of structure I will be employed in a weight ratio to biguanide within the range from about 0.01:1 to about 100:1, preferably from about 0.5:1 to about 2:1.

The antidiabetic agent may also preferably be a sulfonylurea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred.

The compounds of structure I will be employed in a weight ratio to the sulfonyl urea in the range from about 0.01:1 to about 100:1, preferably from about 0.2:1 to about 10:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in a separate oral dosage form.

The compounds of structure I will be employed in a weight ratio to the glucosidase inhibitor within the range from about 0.01:1 to about 100:1, preferably from about 0.5:1 to about 50:1.

The compounds of structure I may be employed in combination with a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GI-262570, englitazone (CP-68722, Pfizer), or darglitazone (CP-86325, Pfizer).

The compounds of structure I will be employed in a weight ratio to the thiazolidinedione in an amount within the range from about 0.01:1 to about 100:1, preferably from about 0.5:1 to about 5:1.

The sulfonylurea and thiazolidinedione in amounts of less than about 150 mg oral antidiabetic agent may be incorporated in a single tablet with the compounds of structure I.

The compounds of structure I may also be employed in combination with a non-oral antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices.

Where present, metformin, the sulfonylureas, such as glyburide, glimepiride, glipyride, glipizide, chlorpropamide and gliclazide and the glucosidase inhibitors acarbose or miglitol or insulin may be employed in formulations as described above and in amounts and dosing as indicated in the Physician's Desk Reference.

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (TheraTech), U.S. Pat. No. 5,614,492 and U.S. Pat. No. 5,631,224 which are incorporated herein by reference.

The antidiabetic agent may also be a PPAR α/γ dual agonist such as disclosed by Murakami et al, "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998).

The antidiabetic agent may be an aP2 inhibitor such as disclosed in U.S. application Ser. No. 09/391,053, filed Sep. 7, 1999, and U.S. provisional application No. 60/127,745, filed Apr. 5, 1999, employing dosages as set out herein.

The antidiabetic agent may be an SGLT2 inhibitor such as disclosed in U.S. provisional application 60/158,773 filed Oct. 12, 1999.

The compounds of formula I will be employed in a weight ratio to the PPAR α agonist, PPAR γ agonist, PPAR γ/α dual agonists, SGLT2 inhibitor and/or aP2 inhibitor within the range from about 0.01:1 to about 100:1, preferably from about 0.5:1 to about 5:1.

The dose administered must be carefully adjusted according to age, weight and condition of the patient, as well as the route of administration, dosage form and regimen and the desired result.

The dosages and formulations for the hypolipidemic agent and antidiabetic agent will be as disclosed in the various patents and applications discussed above and in the PDR.

The dosages and formulations for the other hypolipidemic agent, antidepressant, bone resorption inhibitor, appetite suppressant and anti-obesity agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 100 mg/kg and preferably from about 0.1 mg/kg to about 75 mg/kg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For parenteral administration, the MTP inhibitor will be employed in an amount within the range of from about 0.005 mg/kg to about 10 mg/kg and preferably from about 0.005 mg/kg to about 8 mg/kg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The compounds of formula I and the hypolipidemic agent, antidepressant or bone resorption inhibitor may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin.

The compounds of formula I of the invention can be administered orally or parenterally such as subcutaneously or intravenously, as well as by nasal application, rectally or sublingually to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, ointment, hydrophilic ointment, cream, lotion, solution or suspension or in other type carrier materials such as transdermal devices, iontophoretic devices, rectal suppositories, inhalant devices and the like. The composition or carrier will contain about 5 to about 500 mg per unit of dosage of a compound of formula I. They may be compounded in conventional matter with a physiologically acceptable vehicle or carrier, excipient, binder, preservative, stabilizer, and flavor, as called for by accepted pharmaceutical practice.

The following working Examples represent preferred embodiments of the present invention.

EXAMPLE 1

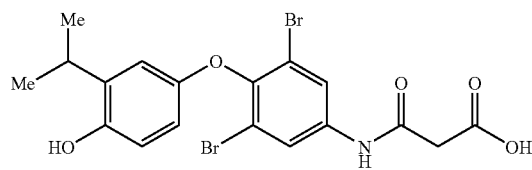

3-[[3,5-dibromo-[4-hydroxy-3-(1-methylethyl)phenoxy]-phenyl]amino]-3-oxopropanoic acid Compound 1a:

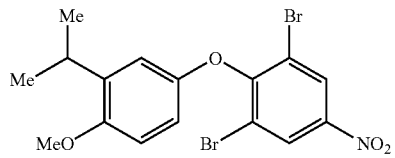

Bis(3-isopropyl-4-methoxyphenyl)iodonium tetrafluoroborate (32.8 g, 64 mmol), 2,6-dibromo-4-nitrophenol (12.6 g, 42 mmol), and Cu powder [Lancaster 300 mesh (6.8 g, 108 mmol)] were suspended in 400 ml of $CH_2Cl_2$ in a flask covered with aluminum foil. While stirring, triethylamine (18.4 mL, 219 mmol) was added and the reaction mixture was stirred under argon in the dark for 4 days. The crude reaction mixture was concentrated to about 70 mL and then chromatographed in two portions through 1.8 liters each of Merck silica gel with 3% to 5% ethyl acetate in hexanes. The combined yield of compound 1a was 15.4 g (81.9%).

Compound 1b:

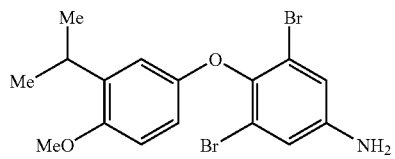

Compound 1a (15.2 g), 34.15 mmol) was dissolved in 129 mL of glacial acetic acid and 13 mL of water. Iron powder (Aldrich <10 micron, 12 g, 215 mmol) was added and the reaction was stirred under argon overnight. The reaction mixture was filtered through Celite and the pad was washed through with about 50 mL of acetic acid. The filtrate was concentrated to about 60 mL and poured onto 400 g of $Na_2CO_3$. Water (400 mL) was added and the product was extracted with ethyl acetate (3×500 mL each). The ethyl acetate was concentrated in vacuo and the residue (13.2 g) was chromatographed through 1.8 liters of Merck silica gel using an ethyl acetate:hexane mixture (8:2). Compound 1b (8.75 g) was obtained in 61.7% yield as a solid. Proton and carbon NMR were consistent with the desired structure.

Compound 1c:

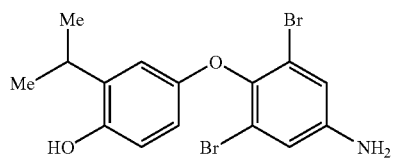

Compound 1b (8.1 g, 19.7 mmol) was dissolved in 20 mL of dichloromethane and this solution was added dropwise to a precooled (about −60° C.) solution of $BBr_3$ (18 mL, ca. 10 equivalents) in 180 mL of dichloromethane under argon. At this low temperature a solid precipitated out. The reaction was allowed to warm up slowly to 0° C. and then stirred at 0° C. for one hour. The reaction was diluted with 200 mL of $CH_2Cl_2$ and quenched by pouring into a cooled, vigorously stirred solution of saturated aqueous $Na_2CO_3$ (300 mL) and $CH_2Cl_2$ (300 mL). The organic layer was separated, diluted with 100 mL of MeOH and concentrated in vacuo and taken up in MeOH (100 mL) and re-concentrated three times. The residue was dissolved in 400 mL of EtOAc, washed 2× with sat'd $NaHCO_3$, brine, dried ($Na_2SO_4$), filtered and concentrated in vacuo to yield 1c as a solid (7.2 g, 91% yield). Proton and carbon NMR were consistent with the desired structure.

Compound 1d:

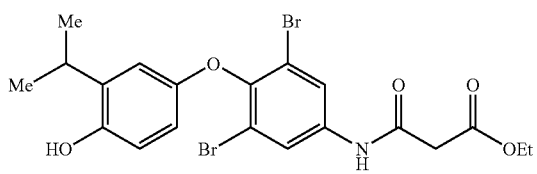

Compound 1c (6.23 g, 15.5 mmol), malonic acid monoethyl ester (2.9 g, 22 mmol), N-methylmorpholine (1.75 mL, 15.8 mmol) and hydroxy-7-azabenzotriazole (3.1 g, 23 mmol) were partially dissolved in 200 mL of $CH_2Cl_2$. This reaction was cooled to 0° C. and (1-[3-(dimethylamino)propyl]-3-ethylcarbodiimide, hydrochloride (4.4 g, 23 mmol) was added and the reaction was stirred for 2 hours. The reaction mixture was diluted with 200 mL of $CH_2Cl_2$ and washed with water, saturated aqueous $NaHCO_3$, brine, dried with $Na_2SO_4$, filtered and concentrated. The crude product was chromatographed in 2 batches through 300 g each of Merck silica gel using 30% ethyl acetate in hexanes. Intermediate fractions were pooled and concentrated to yield 5.3 g (66.7%) of pure product. Late and early fractions were combined 0.96 g of product 1d contaminated slightly with starting malonate and an unknown impurity.

EXAMPLE 1:

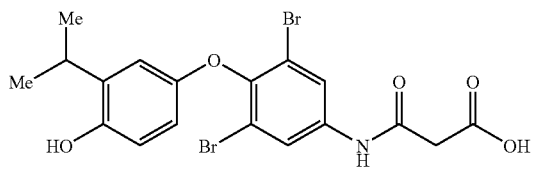

The malonic ester 1d (5.180 g, 9.91 mmol) was dissolved in 29.5 mL of methanol and cooled to 0° C. Then 29.7 mL of 1N sodium hydroxide (29.73 mmol, 3 equiv.) was added to the reaction over 5 minutes and the reaction was allowed to warm to room temperature. After 15 minutes, the methanol was removed under vacuum. Then the remaining basic solution was diluted with 29.7 mL of water and cooled in an ice bath. To the basic solution was added 1N hydrochloric acid dropwise until the pH was 1. The resulting white semi-solid was collected on a large fritted funnel. The solid was washed 5 times with cold water, then dried over potassium hydroxide for 3 days in vacuo. The final weight of the title compound was 5.01 g (99% yield). The product gave consistent mass spectral data.

$^1$H NMR (500 MHz, Acetone-D6, δ): 8.07 (s, 2H), 6.75 (m, 2H), 6.37 (dd, 1H, J=8.8, 3.3 Hz), 3.51 (s, 2H), 3.28 (q, 1H, J=6.5 Hz), 1.17 (d, 6H, J=7.1 Hz) $^{13}$C NMR (500 MHz, Methanol-D3, δ): 171.06, 167.36, 151.54, 150.59, 147.15, 138.30, 137.47, 125.04, 119.54, 116.34, 114.14, 113.14, 41.98, 28.15, 22.80 Elemental Analysis consistent with $C_{18}H_{17}Br_2NO_5 \cdot 1.75\ H_2O$: C, 41.68%; H, 3.89%; N, 2.63%; Br, 30.70%.

EXAMPLE 2

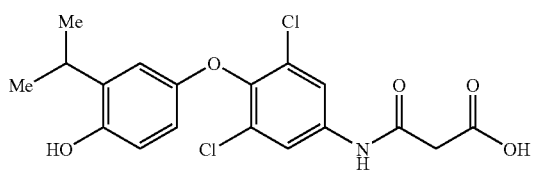

3-[[3,5-dichloro-[4-hydroxy-3-(1-methylethyl)phenoxy]-phenyl]amino]-3-oxopropanoic acid Compound 2a:

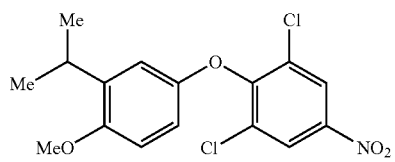

Bis-(3-isopropyl-4-methoxyphenyl)iodonium tetrafluoroborate (15.0 g, 29.4 mmol), 2,6-dichloro-4-nitrophenol (4.16 g, 20 mmol), and Cu powder [Lancaster 300 mesh (3.2 g, 50 mmol)] were suspended in 200 mL of $CH_2Cl_2$ in a flask covered with aluminum foil. While stirring, triethylamine (8.4 mL, 100 mmol) was added and the reaction mixture was stirred under argon in the dark for 5 days. The crude reaction mixture was concentrated to about 50 mL and then chromatographed through 2.0 liters of Merck silica gel with 3% ethyl acetate in hexanes. The combined yield of compound 2a was 4.9 g (68.8%). The product gave a consistent proton NMR spectrum.

Compound 2b:

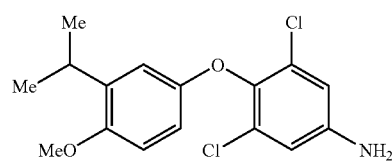

Compound 2a (4.9 g, 13.8 mmol) was dissolved in 80 mL of glacial acetic acid and 8 mL of water. Iron powder (Aldrich <10 micron, 4.6 g, 81.6 mmol) was added and the reaction was stirred under argon overnight. The reaction mixture was filtered through Celite and the pad was washed thoroughly with about 50 mL of methanol. The filtrate was concentrated in vacuo. Saturated $Na_2CO_3$ (400 mL) was added and the product was extracted with ethyl acetate (3×500 mL each). The ethyl acetate extract was concentrated in vacuo and the residue was chromatographed through 1.8 liters of Merck silica gel using an ethyl acetate:hexanes mixture (8:2). Compound 2b (2.2 g) was obtained in 49.4% yield as a solid. Proton and carbon NMR were consistent with the desired structure.

Compound 2c:

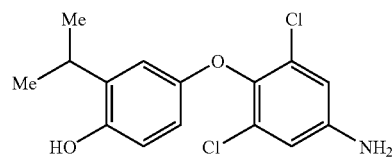

Compound 2b (1.8 g, 5.65 mmol) was dissolved in 15 mL of dichloromethane and this solution was added dropwise to a precooled (about −60° C.) solution of $BBr_3$ (5.3 mL, 56.5 mmol) in 40 mL of dichloromethane under argon. At this low temperature a solid precipitated out. The reaction was allowed to warm up slowly to 0° C. and then stirred at 0° C. for one hour. The reaction was diluted with 200 mL of $CH_2Cl_2$ and quenched by pouring into a cooled, vigorously stirred solution of saturated aqueous $Na_2CO_3$ (200 mL) and $CH_2Cl_2$ (200 mL). The organic layer was separated, diluted with 100 mL of MeOH and concentrated in vacuo and 3× from MeOH (50 mL each). The residue was dissolved in 300 mL of EtOAc, washed 2× with sat'd $NaHCO_3$, brine, dried ($Na_2SO_4$), filtered and concentrated in vacuo to yield compound 2c as a solid (1.77 g, 99% yield). Proton and carbon NMR were consistent with the desired structure.

Compound 2d:

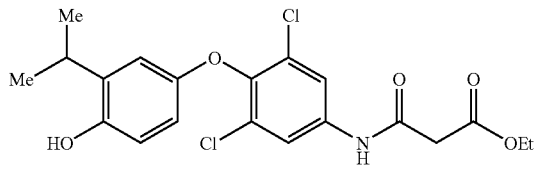

To a mixture of the compound 2c (700 mg, 2.24 mmol), ethyl hydrogen malonate (440 mg, 3.32 mmol), 1-[3-(dimethylamino)propyl]-3-ethylcarbodiimide, hydrochloride (632 mg, 3.33 mmol), 1-hydroxybenzotriazole (450 mg, 3.40 mmol) in $CH_2Cl_2$ (24 mL) cooled with an ice-water bath was added N-methylmorpholine (41 µL, 2,46 mmol). The temperature was allowed to warm up to room temperature and left to stir overnight (ca. 18 h) under argon. The mixture was diluted with 30 mL of $CH_2Cl_2$ and then washed successively with $H_2O$ (3×100 mL), 1N HCl (3×150 mL), saturated $NaHCO_3$ (3×120 mL) and brine (1×150 mL). The $CH_2Cl_2$ layer was dried over ($Na_2SO_4$) and concentrated in vacuum to give 632 mg of white foam. The crude product was purified by chromatography (75 g silica gel, 20% EtOAc in hexane) to give 500 mg (52%) of purified compound 2d as a white solid. Proton and carbon NMR and LC/MS were consistent with the product.

EXAMPLE 2:

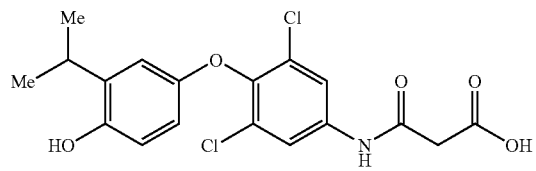

To a solution of compound 2d (330 mg, 0.78 mmol) in methyl alcohol (3.9 mL) was added 1N aqueous sodium hydroxide solution (2.3 mL, 2.3 mmol). After 20 minutes, the mixture was concentrated in vacuo to an aqueous solution that was diluted with 3.2 mL of distilled water. The solution was cooled to 0° C. and acidified with 1N HCl dropwise, until the pH was 1. A white precipitate was collected and dried under vacuum over potassium hydroxide for 18 hours to yield 288 mg (74%) of the title compound as a white solid. Proton and carbon NMR, and LC/MS were consistent with the desired product.

EXAMPLE 3

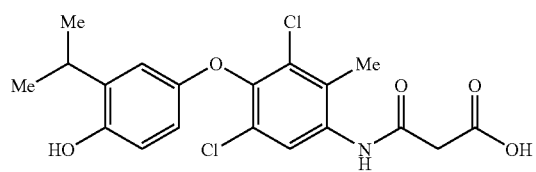

3-[[3,5-dichloro-[4-hydroxy-3-(1-methylethyl)phenoxy]-2-methylphenyl]amino]-3-oxopropanoic acid Compound 3a:

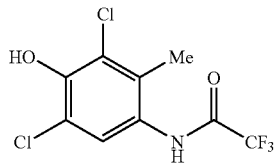

To a solution of 4-amino-2,6-dichloro-3-methylphenol (0.70 g, 3.64 mmol) in anhydrous THF (18 mL) cooled with an ice-water bath was added trifluoroacetic anhydride (0.92 mg, 0.62 mL, 4.39 mmol). The mixture was allowed to warm up to RT. After one hour, the mixture was taken up in EtOAc (50 mL) and then washed with brine (2×25 mL). The EtOAc extract was dried ($Na_2SO_4$), filtered, concentrated and dried in vacuo to give 1.07 g of crude product. The crude product was purified by chromatography (50 g silica gel, 20% EtOAc in hexane) to give 0.93 mg (89%) of compound 3a as a light orange solid.

$^1$H NMR (500 MHz, CD3OD, δ) 7.22 (s, 1H), 2.22 (s, 3H) LC-MS ESI$^-$ [M–H]$^-$=286, 288, 290 (100:64:10)

Compound 3b:

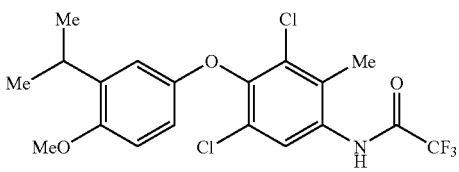

To a mixture of the bis(3-isopropyl-4-methoxyphenyl) iodonium tetrafluoroborate (3.11 g, 6.07 mmol) and copper (0.31 g, 4.86 mmol) in $CH_2Cl_2$ (12 mL) was added a solution of compound 3a (0.70 g, 2.43 mmol) and triethylamine (0.49 g, 0.68 mL, 4.88 mmol) in $CH_2Cl_2$ (12 mL). The mixture was left to stir in the dark at room temperature under $N_2$ for 92 h. The mixture was filtered through a short pad of celite and the filtrate was concentrated in vacuo. The crude product was purified by chromatography (200 g silica gel, 10% EtOAc in hexane) to give 0.42 g (40%) of compound 3b as a light orange solid.

$^1$H NMR (500 MHz, CDCl3, δ): 7.83 (s, 1H), 7.74 (broad s, 1H), 6.86 (d, 1H, J=2.6 Hz), 6.68 (d, 1H, J=8.7 Hz), 6.4 (dd, 1H, J=8.7, 3 Hz), 3.77 (s, 3H), 3.27 (m, 1H), 2.36 (s, 3H), 1.18 (d, 6H, J=7 Hz) LC-MS ESI$^-$ [M–H]$^-$=434, 436, 438 (100:64:10)

Compound 3c:

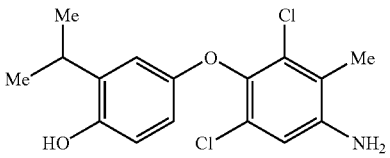

To a solution of compound 3b (243 mg, 0.557 mmol) in glacial acetic acid was added aqueous 48% HBr solution (5 mL). The mixture was heated to 120° C. and maintained at this temperature for 2 h. The mixture was cooled down to ambient temperature and then concentrated in vacuo. The concentrate was taken up in EtOAc (75 mL) and then the pH was adjusted to 7 with saturated aqueous NaHCO$_3$ solution. The EtOAc layer was washed with brine (2×25 mL), dried (MgSO$_4$), filtered, concentrated and dried in vacuo to give 179 mg of purplish solid crude product. The crude product was purified by chromatography (25 g silica gel, 25% EtOAc in hexane) to give 117.2 mg (64%) of compound 3c as a white solid.

$^1$H NMR (500 MHz, CD3OD, δ) 6.78 (s, 1H), 6.60 (d, 1H, J=3.3 Hz), 6.58 (d, 1H, J=8.8 Hz), 6.28 (dd, 1H, J=8.8, 3.3 Hz), 3.21 (m, 1H), 2.20 (s, 3H), 1.14 (d, 6H, J=6.6 Hz) LC-MS ESI$^-$ [M–H]$^-$=324, 326, 328 (100:64:10)

Compound 3d:

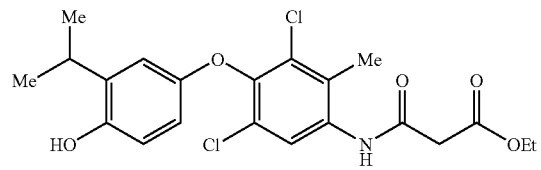

To a mixture of compound 3c (78 mg, 0.24 mmol), ethyl hydrogen malonate (47 mg, 0.36 mmol), 1-[3-(dimethylamino)propyl]-3-ethylcarbodiimide hydrochloride (69 mg, 0.36 mmol), 1-hydroxybenzotriazole (48 mg, 0.36 mmol) in CH$_2$Cl$_2$ (5 mL) cooled with an ice-water bath was added N-methylmorpholine (25 mg, 27 μL, 0.24 mmol). The temperature was allowed to warm up to room temperature and left to stir overnight (ca. 18 h) under N$_2$. The mixture was taken up in EtOAc (50 mL) and then washed successively with H$_2$O (2×20 mL), 1N HCl (2×20 mL), saturated NaHCO$_3$ (2×25 mL), and brine (2×25 mL). The EtOAc layer was dried (MgSO$_4$), filtered and concentrated in vacuo to give 136 mg of slightly pinkish thick oil as crude product. The crude product was purified by chromatography (25 g silica gel, 30% EtOAc in hexane) to give 82 mg (78%) of compound 3d as a white solid.

$^1$H NMR (500 MHz, CDCl3, δ) 9.56 (s, 1H), 8.10 (s, 1H), 6.82 (d, 1H, J=3.3 Hz), 6.60 (d, 1H, J=8.3 Hz), 6.34 (dd, 1H, J=8.8, 2.8 Hz), 4.53 (s, 1H), 4.28(q, 2H, J=7.1 Hz), 3.53 (s, 2H), 3.15 (m, 1H), 2.38 (s, 3H), 1.34 (t, 3H, J=7.2 Hz), 1.22 (d, 6H, J=6.6 Hz) LC-MS ESI$^-$ [M–H]$^-$ =438, 440, 442 (100:64:10)

EXAMPLE 3:

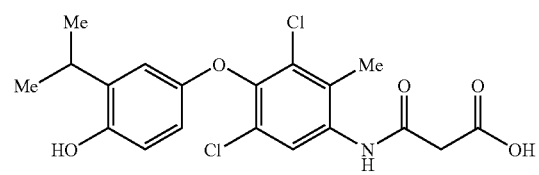

To a solution of compound 3d (70 mg, 0.16 mmol) in THF (1.5 mL) was added 1N aqueous lithium hydroxide solution (0.5 mL, 0.5 mmol). After one hour, the mixture was acidified with 1N HCl and then extracted with EtOAc (50 mL). The EtOAc extract was washed with brine (2×20 mL), dried (Na$_2$SO$_4$), filtered and concentrated in vacuo to give 57 mg of slightly yellowish solid. The crude product showed a small trace of impurity so it was purified by preparative reverse-phase HPLC [gradient solvent system, from 50% B:50% A to 0% A:100% B (A=90% H$_2$O/10% MeOH+0.1% TFA, B=90% MeOH/10% H$_2$O+0.1% TFA) for 10 min, YMC ODS 20×100 mm column] to give 40 mg (61% ) of the title compound as a white solid.

$^1$H NMR (500 MHz, CD3OD, δ) 7.59 (s, 1H), 6.67 (d, 1H, J=2.7 Hz), 6.60 (d, 1H, J=8.8 Hz), 6.30 (dd, 1H, J=8.8, 3.3 Hz), 3.50 (s, 2H), 3.23 (m, 1H), 2.34 (s, 3H), 1.16 (d, 6H, J=6.6 Hz) MS ESI$^-$ [M–H]$^-$=410, 412, 414 (100:64:10)

EXAMPLE 4

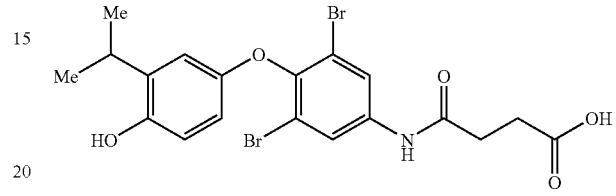

4-[[3,5-dichloro-[4-hydroxy-3-(1-methylethyl)phenoxy]-phenyl]amino]-4-oxobutanoic acid Compound 4a:

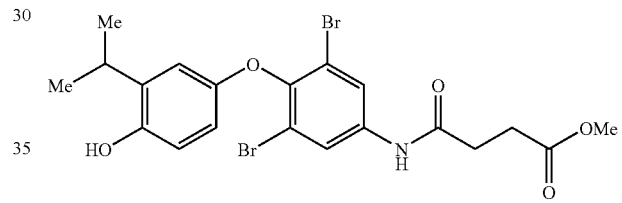

To a pre-cooled –78° C. solution of compound 1c (50 mg, 0.125 mmol) in CH$_2$Cl$_2$ (500 μL) was added triethylamine (26 μL ml, 0.18 mmol). Then 3-carbomethoxypropionyl chloride (16 μL, 0.14 mmol) was added dropwise. The reaction was stirred for two hours. The solution was warmed to room temperature and concentrated in vacuo to yield 26 mg of a brown oil. This crude product was then passed through a 2 gram plug of silica gel with ethyl acetate. The ethyl acetate was concentrated in vacuo to yield 40 mg (63% yield) of compound 4a as a yellow oil. Proton NMR and LC/MS was consistent for the product contaminated by di-acylated by-product.

EXAMPLE 4:

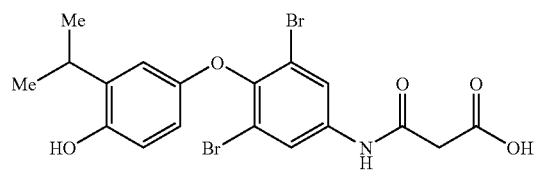

To a solution of compound 4a (23 mg, 0.045 mmol) in methanol (1.5 mL) was added 1N aqueous sodium hydroxide solution (0.08 mL, 0.08mmol). After 3 hours, the mixture was concentrated in vacuo. The reaction was cooled in an ice water bath and 1N HCl was added until the pH was 1. The aqueous solution was extracted with ethyl acetate (3×30 mL). The combined ethyl acetate layers were washed with brine (2×30 mL) and dried over Na$_2$SO$_4$. The ethyl acetate layers were concentrated in vacuo to yield 15 mg of white semi-solid. The crude material was purified by preparative reverse-phase HPLC [gradient solvent system, from 50% A:50% B to 0% A:100% B (A=90% H$_2$O/10% MeOH+0.1% TFA, B=90% MeOH/10% H$_2$O+0.1% TFA) for 15 minutes, YMC ODS 20×100 mm column] to give 8.0 mg (36%) of the title compound as a white solid. Proton NMR and LC/MS were consistent with the desired product.

EXAMPLE 5

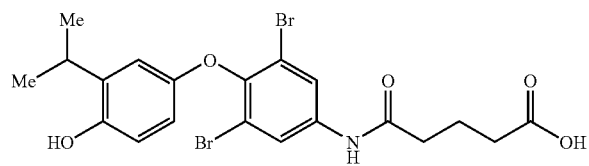

5-[[3,5-dichloro-[4-hydroxy-3-(1-methylethyl)phenoxy]-phenyl]amino]-5-oxopentanoic acid By the procedures described above for Example 4, 15.0 mg (36% yield) of the title compound was obtained as a white solid. Proton NMR and LC/MS were consistent with the desired structure.

EXAMPLE 6

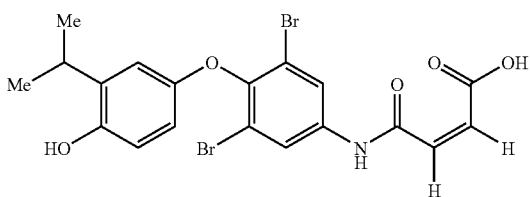

Compound 6a:

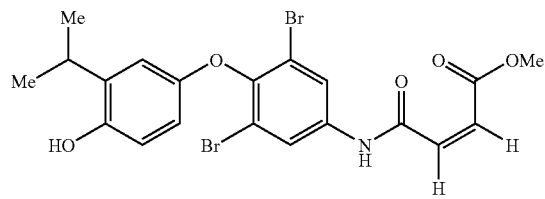

To a mixture of compound 1c (40 mg, 010 mmol), maleic acid, mono-methyl ester (36 μL, 0.29 mmol), 1-[3-(dimethylamino)propyl]-3-ethylcarbodiimide, hydrochloride (72 mg, 0.38 mmol), 1-hydroxybenzotriazole (54 mg, 0.40 mmol) in CH$_2$Cl$_2$ (50 μL) cooled with an ice water bath was added triethylamine (46 μL, 0.28 mmol). The temperature was allowed to warm up to room temperature and left to stir overnight (ca. 18 h) under nitrogen. The mixture was taken up in EtOAc (50 mL) and then washed successively with H$_2$O (2×20 mL), 1N HCl (2×20 mL) saturated NaHCO$_3$ (2×25 mL) and brine (2×25 mL). The EtOAc layer was dried (Na$_2$SO$_4$), and concentrated in vacuo to give 30 mg (58%) of slightly pinkish thick oil as crude product. This was carried on to the hydrolysis step. The proton NMR and LC/MS were consistent for the desired product.

EXAMPLE 6:

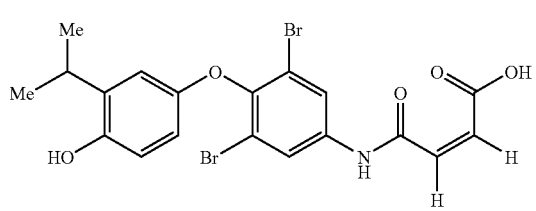

To a solution of compound 6a (15 mg, 0.029 mmol) in methyl alcohol (1.5 mL) was added 1N aqueous sodium hydroxide solution (0.08 mL, 0.08 mmol). After 3 hours, the reaction mixture was concentrated in vacuo to remove methanol. The resulting solution was cooled in an ice water bath and 1N HCl was added until the pH was 1. The aqueous solution was extracted with ethyl acetate (3×30 mL). The combined ethyl acetate layers were washed with brine (2×30 mL) and dried over Na$_2$SO$_4$. The ethyl acetate extract was concentrated in vacuo to yield 12 mg of white semi-solid. The crude material was purified by preparative reverse-phase HPLC [gradient solvent system, from 50% A:50% B to 0% A:100% B (A=90% H$_2$O/10% MeOH+0.1% TFA, B=90% MeOH/10% H$_2$O+0.1% TFA) for 15 minutes, YMC ODS 20×100 mm column] to give 7.9 mg (53%) of the title compound as a white solid. The proton NMR and LC/MS were consistent for the desired structure.

EXAMPLE 7

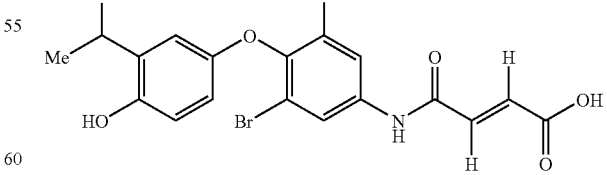

By the procedures described above for Example 6, 17.9 mg (46%) of the title compound was obtained as a white solid. Proton NMR and LC/MS were consistent with the desired structure.

EXAMPLE 8–19

By appropriate application of the procedures described above combined with those described for analogous examples found in "Novel Thyroid Receptor Ligands and Methods", Y.-L. Li, Y. Liu, A. Hedfors, J. Malm, C. Mellin, M. Zhang, PCT Int. App. WO 9900353 A1 990107, the Examples 8–19 described in the table below are prepared.

| Example | R2 | R3 |
|---|---|---|
| 8 | Me | Me |
| 9 | Me | Br |
| 10 | Me | Cl |
| 11 | Me | I |
| 12 | Br | Cl |
| 13 | Br | I |
| 14 | Cl | I |
| 15 | I | I |
| 16 | H | Me |
| 17 | H | Br |
| 18 | H | Cl |
| 19 | H | I |

What is claimed is:

1. A method for treating obesity, hypercolesterolemia atherosclerosis, depression, osteoporosis, hypothyroidism, goiter, glaucoma, cardiac arrhythmia, congestive heart failure, or a skin disorder or disease, which comprises administering to a patient in need of treatment a therapeutically effective amount of a compound of the formula wherein
X is oxygen (—O—), sulfur (—S—), carbonyl (—CO—), methylene (—$CH_2$—), or —NH—;
Y is —$(CH_2)_n$— where n is an integer from 1 to 5, or —C═C—, which is cis or trans;
$R_1$ is halogen, trifluoromethyl, or alkyl of 1 to 6 carbons or cycloalkyl of 3 to 7 carbons;
$R_2$ and $R_3$ are the same or different and are hydrogen, halogen, alkyl of 1 to 4 carbons or cycloalkyl of 3 to 6 carbons, at least one of $R_2$ and $R_3$ being other than hydrogen;
$R_4$ is hydrogen or lower alkyl;
$R_5$ is hydrogen or lower alkyl;
$R_6$ is carboxylic acid, or ester thereof, or a prodrug thereof;
$R_7$ is hydrogen, or an alkanoyl or aroyl group, or other group capable of bioconversion to generate the free phenol structure (wherein $R_7$=H);
including all stereoisomers thereof, a prodrug thereof, or a pharmaceutically acceptable salt thereof.

2. A pharmaceutical composition comprising an effective amount of a compound of the formula wherein
X is oxygen (—O—), sulfur (—S—), carbonyl (—CO—), methylene (—$CH_2$—), or —NH—;
Y is —$(CH_2)_n$— where n is an integer from 1 to 5, or —C═C—, which is cis or trans;
$R_1$ is halogen, trifluoromethyl, or alkyl of 1 to 6 carbons or cycloalkyl of 3 to 7 carbons;
$R_2$ and $R_3$ are the same or different and are hydrogen, halogen, alkyl of 1 to 4 carbons or cycloalkyl of 3 to 6 carbons, at least one of $R_2$ and $R_3$ being other than hydrogen;
$R_4$ is hydrogen or lower alkyl;
$R_5$ is hydrogen or lower alkyl;
$R_6$ is carboxylic acid, or ester thereof, or a prodrug thereof;
$R_7$ is hydrogen, or an alkanoyl or aroyl group, or other group capable of bioconversion to generate the free phenol structure (wherein $R_7$=H);
including all stereoisomers thereof, a prodrug thereof, or a pharmaceutically acceptable salt thereof, together with a pharmaceutically acceptable carrier.

3. A method to treat skin disorder or disease by the use of a compound of the formula wherein
X is oxygen (—O—), sulfur (—S—), carbonyl (—CO—), methylene (—$CH_2$—), or —NH—;
Y is —$(CH_2)_n$— where n is an integer from 1 to 5, or —C═C—, which is cis or trans;
$R_1$ is halogen, trifluoromethyl, or alkyl of 1 to 6 carbons or cycloalkyl of 3 to 7 carbons;

R₂ and R₃ are the same or different and are hydrogen, halogen, alkyl of 1 to 4 carbons or cycloalkyl of 3 to 6 carbons, at least one of R₂ and R₃ being other than hydrogen;

R₄ is hydrogen or lower alkyl;
R₅ is hydrogen or lower alkyl;
R₆ is carboxylic acid, or ester thereof, or a prodrug thereof;
R₇ is hydrogen, or an alkanoyl or aroyl group, or other group capable of bioconversion to generate the free phenol structure (wherein R₇=H);

including all stereoisomers thereof, a prodrug thereof, or a pharmaceutically acceptable salt thereof in combination with a retinoid or a vitamin D analog.

4. The method according to claim 3, in which the skin disorder or disease is dermal atrophy, post surgical bruising caused by laser resurfacing, keloids, stria, cellulite, roughened skin, actinic skin damage, lichen planus, ichtyosis, acne, psoriasis, Dernier's disease, eczema, atopic dermatitis, chloracne, pityriasis and skin scarring.

5. The method as defined in claim 1 where in the compound administered X is oxygen, R₅ is hydrogen, R₁ is isopropyl, R₄ is hydrogen or methyl, R₂ and R₃ are each independently halogen or an alkyl group or hydrogen.

6. The method as defined in claim 5 where in the compound administered one of R₂ and R₃ is halogen and the other is an alkyl group, or wherein one of R₂ and R₃ is halogen and the other is hydrogen, or wherein one of R₂ and R₃ is alkyl and the other is hydrogen.

7. The method as defined in claim 5 where in the compound administered R₂ and R₃ are independently Cl, Br, methyl or ethyl.

8. The method as defined in claim 5 where in the compound administered Y is
—(CH₂)ₙ— where n is 1 or 2 or wherein Y is cis- or trans-ethylene.

9. The method as defined in claim 5 where the compound administered has the structure

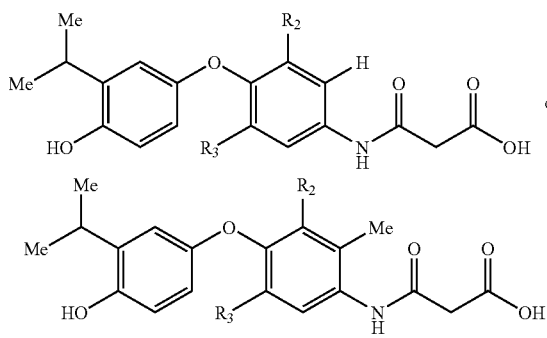

or an alkyl ester thereof.

10. The method as defined in claim 1 wherein the compound administered has the structure

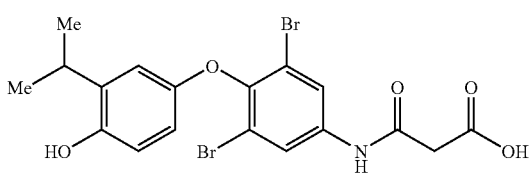

or an alkyl ester thereof.

11. The method as defined in claim 1 wherein the compound administered has the structure

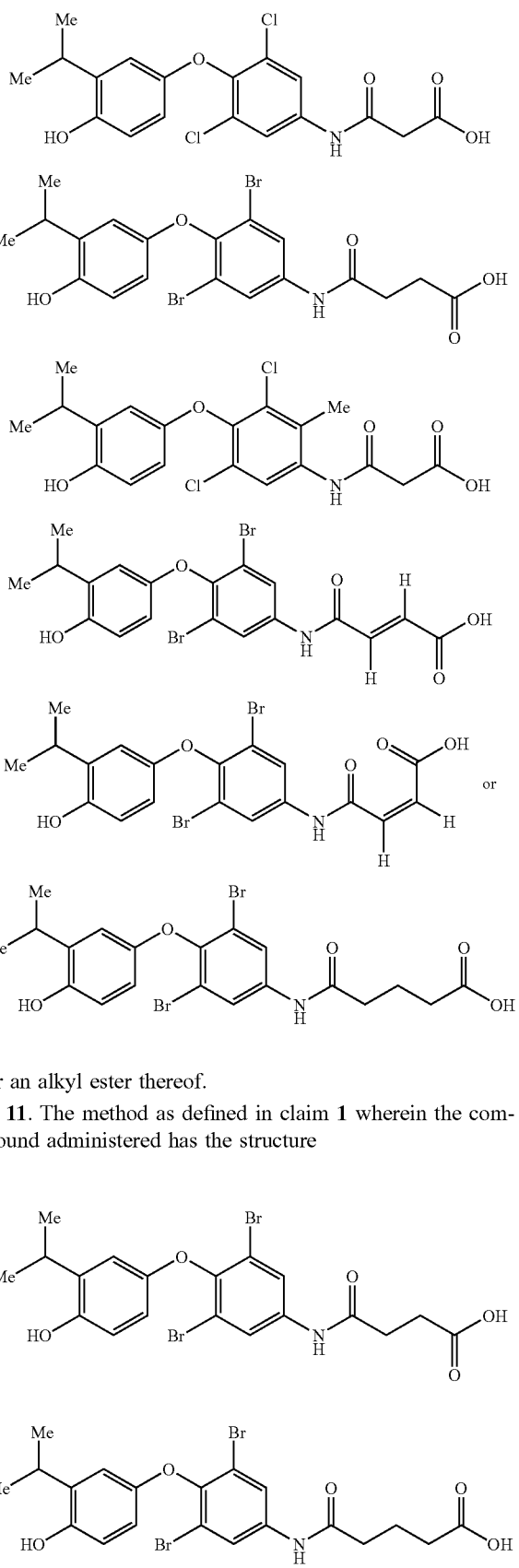

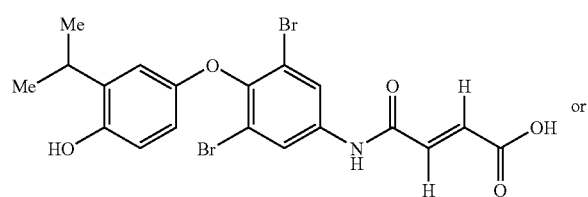
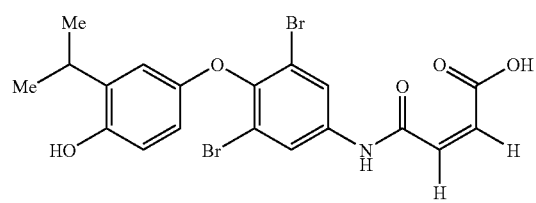
or an alkyl ester thereof.
12. The method as defined in claim 1 wherein the compound administered has the structure
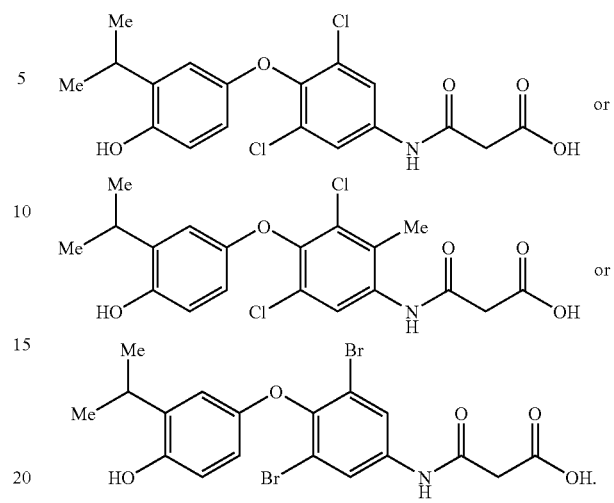
* * * * *